United States Patent
Turkel et al.

(10) Patent No.: US 10,537,619 B2
(45) Date of Patent: Jan. 21, 2020

(54) METHODS FOR TREATING OSTEOARTHRITIS PAIN

(71) Applicant: Allergan, Inc., Irvine, CA (US)

(72) Inventors: Catherine C. Turkel, Newport Coast, CA (US); Guang-Liang Jiang, Irvine, CA (US); Ronald E. DeGryse, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 56 days.

(21) Appl. No.: 14/840,923

(22) Filed: Aug. 31, 2015

(65) Prior Publication Data

US 2016/0074485 A1 Mar. 17, 2016

Related U.S. Application Data

(60) Provisional application No. 62/049,759, filed on Sep. 12, 2014, provisional application No. 62/052,833, filed on Sep. 19, 2014.

(51) Int. Cl.
*A61K 38/48* (2006.01)
*A61K 9/00* (2006.01)

(52) U.S. Cl.
CPC ........ *A61K 38/4893* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 6,306,423 B1 | 10/2001 | Donovan et al. | |
| 6,312,708 B1 | 11/2001 | Donovan | |
| 6,464,986 B1* | 10/2002 | Aoki | A61K 38/4893 424/236.1 |
| 6,585,993 B2 | 7/2003 | Donovan et al. | |
| 8,398,611 B2 | 3/2013 | Hwang et al. | |
| 8,470,337 B2 | 6/2013 | Manack et al. | |
| 2007/0160633 A1* | 7/2007 | First | A61K 31/167 424/239.1 |
| 2009/0232851 A1 | 9/2009 | Auguet et al. | |
| 2016/0074485 A1 | 3/2016 | Turkel et al. | |

FOREIGN PATENT DOCUMENTS

JP 2011042616 3/2011

OTHER PUBLICATIONS

Mahowald et al. "Long term effects of intra-articular botulinum toxin A for refractory joint pain." Neurotoxicity Research 9(2-3): 179-188, 2006.*
Boon et al. "Efficacy of intra-articular botulinum toxin type A in painful knee osteoarthritis: a pilot study" PM&R 2(4): 268-276, 2010.*
Chou et al. "Therapeutic effects of intra-articular botulinum neurotoxin in advanced knee osteoarthritis", Journal of the Chinese Medical Association 73 (11): 573-580, 2010.*
Hochman et al. "The nerve of osteoarthritis pain", Arthritis Care & Research 62(7): 1019-1023, 2010.*
Freynhagen et al. "painDETECT: a new screening questionnaire to identify neuropathic components in patients with back pain", Current Medical Research and Opinion 22(10): 1911-20, 2006.*
Aoki "Evidence for antinociceptive activity of botulinum toxin type A in pain management", Headache: The Journal of Head and Face Pain 43 (s1): 9-15, 2003.*
Perrot "Osteoarthritis pain." Best Practice & Research Clinical Rheumatology 29.1 (2015): 90-97 (Year: 2015).*
Boon, Andrea et al, Efficacy of Intra-Articular Botulinum Toxin Type A in Painful Knee Osteoarthritis: A Pilot Study, Journal of Injury, Function, and Rehabiliation, Apr. 2010, 268-276, 2(4).
Borodic, Gary et al, Clinical and Scientific Aspects of Botulinum A Toxin, Ophthalm Clincs of N America, Sep. 1991, 491-503, 4(3).
Chou, Chen-Liang et al, Therapeutic Effects of Intra-Articular Botulinum Neurotoxin in Advanced Knee Osteoarthritis, J Chin Med Assoc, 2010, 573-580, 73(11).
Cortes Corral, Carmen Eudella et al, Therapeutic Effects of Intraarticular Injection With Botulinum Toxin Type A in Advanced Gonarthrosis, PM&R 8th World Congress of the International Society of Physical & Rehabilitation Medicine, Jun. 2014, S138-S139, 6.
Fenolossa, Vazquez et al, Effects of Intraarticular Botulinum Toxin A BOTOX (R) on Refractory Knee Osteoarthritis, Revista De La Sociedad Espanola Del Dolor, Nov. 2011, 1 Page, 18(6).
Fluchaire, Ethel et al, Randomized Controlled Trial: Decreased Pain and Improved Functionality by Using Intraarticular Injection of Botulinum Toxin Type A Vs Intraarticular Injection With Methylprednlsolone in Knee Osteoarthrosis, Pm&R 8th World Congress of the International Society of Physical & Rehabilitation Medicine, Jun. 2014, S127, 6(8).
Hambleton, Peter, Clostridium botulinum toxins: a general review of involvement in disease, structure,mode of action and preparation for clinical use, Journal of Neurology, 1992, 16-20, 239.
Hdez, Sofia Duran et al, Botulinum Toxin Type A Clinical Effect in Fonarthrosis Grade II Patients, PM&R 8th World Congress of the International Society of Physical & Rehabilitation Medicine, Jun. 2014, S95, 6(8).
Jankovic, Joseph, Therapeutic Uses of Botulinum Toxin, N Engl J Med, 1991, (17):1186-1194.
Schantz, Edward, , Preparation and Characterization of Botulinum Toxin Type A for Human Treatment, Neurological Diseases and Therapy, 1994, Chapter 3, 41-49.
Simpson, Lance, The Origin, Structure, and Pharmacological Activity of Botulinum Toxin, Pharmcol Rev, 1981, 155-188, 33(3).
Singh, Jasvinder et al, Intra-Articular Botulinum Toxin A for Refractory Shoulder Pain: A Randomized, Double-Blinded, Placebo-Controlled Trial, Translational Research, 2009, 205-216, 153.
Dimitroulas, Theodoros et al., Neuropathic pain in osteoarthritis: A reivew of pathophysiological mechanisms and implications for treatment, Seminars in Arthritis and Rheumatism, 2014, pp. 145-154, vol. 44, No. 2.

(Continued)

*Primary Examiner* — Emily A Cordas
(74) *Attorney, Agent, or Firm* — Brigitte C. Phan (57) ABSTRACT

Methods for alleviating osteoarthritis-associated symptoms by selecting a treatment-eligible patient and local administration of a clostridial derivative, such as a botulinum toxin, to an osteoarthritis-affected site are disclosed herein.

8 Claims, 6 Drawing Sheets

(56) References Cited

OTHER PUBLICATIONS

Kalunian, KC et al, Results from a single center, double-blind, randomized placebo-controlled, parallel-group study of the efficacy and safety of intra-articular onabotulinumtoxinA for osteoarthritis knee pain, Osteoarthritis and Cartilage, vol. 22, Supplement, S192, Abstract 330.

Mathieson, Stephanie et al., Neuropathic pain screeing questionnairs have imited measurement properties. A systematic review., 2015, pp. 957-966, vol. 68, No. 8.

Oteo-Alvaro, Angel et al., High Prevalence of Neuropathic Pain Features in Patients with Knee Osteoarthritis: A cross-Sectional Study, Pain Practice, 2015, pp. 618-626, vol. 15, No. 7.

* cited by examiner

METHODS FOR TREATING OSTEOARTHRITIS PAIN

CROSS-REFERENCES TO RELATED APPLICATIONS

This application claims the benefit of U.S. Provisional Applications Ser. Nos. 62/049,759, filed Sep. 12, 2014, and 62/052,833, filed Sep. 19, 2014; all incorporated herein entirely by reference.

FIELD

The present disclosure relates to methods for treatment of arthritis. In particular, the present disclosure relates to methods of treating osteoarthritis-associated symptoms, such as pain, using a clostridial derivative.

BACKGROUND

Arthritis is one of the most prevalent chronic health problems and one of the most common causes of disability in America. It affects over 45 million adults in the United States. This number is anticipated to rise to 60 million, or 18% of the population, by 2020. There are more than 127 different types of arthritis as defined by the Arthritis Foundation, including osteoarthritis, rheumatoid arthritis, psoriatic arthritis, septic arthritis and related autoimmune diseases. Regardless of the type of arthritis, common symptoms for all arthritis disorders include varied levels of pain, swelling, functional limitation and joint stiffness. Arthritic disorders such as lupus and rheumatoid can also affect other organs in the body.

The goals of current therapies for arthritis, including osteoarthritis, are to alleviate pain and other related arthritis associated symptoms. Current therapies for managing osteoarthritis pain include oral analgesics or corticosteroids, localized treatments with topical analgesics (e.g., NSAIDs, capsaicin), intra-articular injections of corticosteroids or viscosupplements. Oral analgesics have substantial limitations because they may not provide sufficient pain relief and often produce intolerable side effects, for example, gastrointestinal bleeding and renal toxicity for regular NSAIDs users, addiction or breathing suppression for opioids; and adverse drug interactions. Localized corticosteroid injections may reduce pain for a short period (1-3weeks), but have long term side effects, including cartilage break down, Cushing's syndrome; furthermore they are intolerable to patients with diabetic mellitus. Viscosupplement administration, such as hyaluronic acid, While well-tolerated, is not always effective. Thus, there is a need for safe, effective alternative therapies for treatment of osteoarthritis pain.

SUMMARY OF THE INVENTION

Aspects of the present disclosure provide a method for treating or alleviating at least one symptom of arthritis, such as osteoarthritis. In some aspects, the present disclosure provides a method for treating or alleviating at least one osteoarthritis-associated symptom, such as OA pain, in a patient in need thereof.

In some aspects, the present disclosure provides a method for treating or alleviating OA-associated pain, the method comprises selecting a treatment-susceptible or treatment-eligible patient, administering to the treatment-eligible patient a therapeutically effective amount of a clostridial derivative to an osteoarthritis-affected site of the treatment-susceptible patient, thereby treating or alleviating the OA-associated pain. In some embodiments, the selecting step comprises categorizing the pain that a patient experiences at the osteoarthritis-affected site, and identifying the patient as treatment-susceptible/eligible. In some embodiments, the identifying step comprises categorizing the OA-associate pain as nociceptive or non-nociceptive, such as neuropathic pain. In some embodiments, the selecting step comprises selecting a patient having nociceptive pain. In some embodiments, the selecting step comprises providing the patient a plurality of questions relating to characteristics of the OA-associated pain that the patient perceives, receiving numerical responses to the plurality of questions by the patient, calculating a score based on the numerical responses, comparing the score to a cut-off value; and determining whether the patient is treatment-eligible.

BRIEF DESCRIPTION OF THE DRAWINGS

The following drawings are presented to illustrate aspects and features of embodiments of the present invention.

DETAILED DESCRIPTION OF THE PREFERRED EMBODIMENTS

Definitions

As used herein, the words or terms set forth below have the following definitions:

"About" or "approximately" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value.

"Administration", or "to administer" means the step of giving (i.e. administering) a *botulinum* toxin to a subject, or alternatively a subject receiving a pharmaceutical composition. The present method can be performed via administration routes including intramuscular, non-intramuscular, intra-articular, extra-articular, peri-articular, intradermal, subcutaneous administration, topical administration (using liquid, cream, gel or tablet formulation), intrathecal administration, intraperitoneal administration, intravenous infusion, implantation (for example, of a slow-release device such as polymeric implant or miniosmotic pump, or combinations thereof.

"Alleviating" means a reduction in arthritis associated structural deterioration. Thus, alleviating includes some reduction, significant reduction, near total reduction, and total reduction. An alleviating effect may not appear clinically for between 1 to 7 days after administration of a clostridial derivative to a patient or sometime thereafter.

"*Botulinum* toxin" means a neurotoxin produced by *Clostridium botulinum*, as well as a *botulinum* toxin (or the light chain or the heavy chain thereof) made recombinantly by a non-Clostridial species. The term "*botulinum* toxin", as used herein, encompasses the *botulinum* toxin serotypes A, B, $C_1$, D, E, F and G, and their subtypes and any other types of subtypes thereof, or any re-engineered proteins, analogs, derivatives, homologs, parts, sub-parts, variants, or versions, in each case, of any of the foregoing. "*Botulinum* toxin", as used herein, also encompasses a "modified *botulinum* toxin". Further "*botulinum* toxin" as used herein also encompasses a *botulinum* toxin complex, (for example, the 300, 600 and 900 kDa complexes), as well as the neurotoxic component of the *botulinum toxin* (150 kDa) that is unassociated with the complex proteins.

"Clostridial derivative" refers to a molecule which contains any part of a clostridial toxin. As used herein, the term "clostridial derivative" encompasses native or recombinant neurotoxins, recombinant modified toxins, fragments thereof, a Targeted vesicular Exocytosis Modulator (TEM), or combinations thereof.

"Clostridial toxin" refers to any toxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate.

"Effective amount" as applied to the biologically active ingredient means that amount of the ingredient which is generally sufficient to induce a desired change in the subject.

"Implant" means a controlled release (e.g., pulsatile or continuous) composition or drug delivery system. The implant can be, for example, injected, inserted or implanted into a human body.

"Intra-articular injection" refers to an injection directly into a joint or into a portal.

"Extra-articular injection" refers to an injection outside of a joint space.

"Nociceptive pain" is defined as pain that arises from actual or potential damage to non-neuronal tissue and is due to the physiological activation of nociceptors.

"Neuropathic pain" is defined as pain arising as a direct consequence of a lesion or disease of the somatosensory nerve system.

"Peri-articular injection" refers to an injection to an area around a joint.

"Local administration" means administration of a clostridial derivative to or to the vicinity of an arthritis-affected site in a patient by a non-systemic route. Thus, local administration excludes systemic routes of administration, such as intravenous or oral administration.

"Peripheral administration" means administration to a location away from a symptomatic location, as opposed to a local administration.

"TEMs", abbreviated for Targeted Exocytosis Modulators are retargeted endopeptidases that direct the catalytic activity of the light chain to specific types of neuronal cells or to target cells that were not affected by *botulinum* toxins expanding the beneficial clinical effect of inhibition of exocytosis in several human diseases.

"Treating" or "treatment" means to alleviate (or to eliminate) an undesirable condition, for example cartilage deterioration, either temporarily or permanently.

"Therapeutically effective amount" refers to an amount sufficient to achieve a desired therapeutic effect. The therapeutically effective amount usually refers to the amount administered per injection site per patient treatment session, unless indicated otherwise.

"Treatment-susceptible", used interchangeably with "treatment-eligible" refers to a patient or a group which is deemed eligible to receive the treatment after the symptoms, such as pain, of the patient or the group have been categorized or classified. In some embodiments, treatment-eligible refers to a patient or group of patient whose pain has been classified as nociceptive pain.

"Treatment-uncertain", refers to a patient or a group which may or may not be eligible to receive the treatment after the symptoms, such as pain, of the patient or the group have been categorized or classified. In some embodiments, treatment-uncertain refers to a patient or group of patients whose pain has been classified as non-nociceptive pain, and the pain is classified as possibly neuropathic pain. In some embodiments, after the classification of nociceptive versus non-nociceptive, an additional categorizing step may be required to decide whether the patient is eligible for treatment.

"Treatment-unsusceptible", used interchangeably with "treatment-ineligible" refers to a patient or a group which is not deemed eligible to receive the treatment after the symptoms, such as pain, of the patient or the group have been categorized or classified. In some embodiments, treatment-ineligible refers to a patient or group of patient whose pain has been classified as non-nociceptive pain. In some embodiments, the treatment-ineligible refers to a patient classified as having neuropathic pain.

In some aspects, the present disclosure provides a method for treating or alleviating arthritis-associated symptoms, including osteoarthritis (OA)-associated pain, rheumatoid arthritis (RA)-associated pain or psoriatic arthritis-associated pain in a patient.

Arthritis

Arthritis is a form of joint disorder that involves inflammation of one or more joints. Normal articular cartilage consists of an extensive hydrated extracellular matrix. The matrix consists mainly of collagen and proteoglycans, principally aggrecan, which is large and aggregates with hyaluronic acid. Embedded in the extracellular matrix are the chondrocytes, which regulate the synthesis and degradation of the articular cartilage. In normal articular cartilage, the extracellular matrix is constantly being degraded and synthesized. Collagen and cartilage proteoglycans are degraded by various proteinases, including metalloproteinases, and collagenases. Under normal circumstances, the activation of these degradative enzymes is held in check by inhibitors, such as tissue inhibitor of metalloproteinases (TIMPs) and plasminogen activator inhibitor-7 (PAI-7). The balance of metalloproteinases (MMPs) and inhibitors of metalloproteinases (TIMPs) is important to maintain the normal turnover of the extracellular matrix. Under pathological conditions such as for example in Osteoarthritis and Rheumatoid arthritis, mechanical and shear stress, inflammatory cytokines (e.g., IL-1, IL-6 and tumor necrosis factor-α) and/or growth factors disrupt this balance and promote the synthesis of MMPs and inhibit the expression of TIMPs. Thus, collagen and aggrecan degradation will outweigh the synthesis and deposition by chondrocytes, which ultimately results in cartilage defect. Inflammation can occur secondary to structural damage as in osteoarthritis or is the main cause to incur arthritis with subsequent structural damage as in rheumatoid arthritis.

Osteoarthritis (OA)

Osteoarthritis (OA) is the most common form of arthritis and a leading cause of chronic disability. It can affect both the larger and the smaller joints of the body, including the hands, feet, back, hip, knee and spine. OA is a multifactorial disease, characterized by joint pain, tenderness, limitation of movement, crepitus, occasional effusion, wear or tear of cartilage, wear or tear of meniscus, wear or tear of ligament, subchondral bone lesion, capsule damage and/or hyperplasia of the synovial membrane. Progression of OA is marked by destruction of the joint cartilage, sclerosis or cyst formation of underlying bone, joint space narrowing and formation of osteophytes at the joint margin. Knee OA is a highly prevalent condition that affects upwards of 89 million people worldwide. Approximately 12.1% of people older than 60 years have symptomatic knee OA. Pain is the most prominent symptom of knee OA and is the primary reason patients seek medical help. Knee OA is often progressive, and currently there is no known cure. The primary goals for treatment include relieving pain, maintaining/improving function and reducing disability. Despite the availability of various pharmacologic agents, symptom management for patients suffering from knee pain and functional disability due to OA continues to be a problem for many due to ineffectiveness and/or intolerability of many of these agents in this patient population. Thus, there is a high unmet medical need for more effective and well-tolerated treatments.

Rheumatoid Arthritis (RA)

Rheumatoid arthritis (RA) is an autoimmune disease that results in a chronic, systemic inflammatory disorder that may affect many tissues and organs, but principally attacks flexible (synovial) joints. It can be a disabling and painful condition, which can lead to substantial loss of functioning and mobility if not adequately treated. Joint cartilage loss and other structural damage are subsequent to inflammatory response at the involved joints. Once cartilage lesion occurs, RA will have a similar disease progression as OA even after the primary inflammation cause is under control.

*Botulinum* Toxin

*Botulinum* neurotoxins (BoNTs) such as, for example, BoNT/A, BoNT/B, etc., act on the nervous system by blocking the release of neurosecretory substances such as neurotransmitters at the nerve endings. The action of BoNT is initiated by its binding to a receptor molecule on the cell surface, then the toxin-receptor complex undergoes endocytosis. Once inside the cell, BoNT cleaves exocytotic specific proteins responsible for neurotransmitter docking and release from the cell known as the SNARE proteins (soluble N-ethylmaleimide-sensitive factor attachment protein receptor). The resulting transient chemodenervation has been utilized medically to block motor neurotransmission at the neuromuscular junction leading to a variety of therapeutic applications.

Of the existing serotypes, *Botulinum* toxin type A is one of the most lethal natural biological agents known to man. About 50 picograms of a commercially available *botulinum* toxin type A (purified neurotoxin complex, available from Allergan, Inc., of Irvine, Calif. under the trade name BOTOX® in 100 unit vials) is a $LD_{50}$ in mice (i.e. 1 unit). One unit of BOTOX® contains about 50 picograms (about 56 attomoles) of *botulinum* toxin type A complex. One unit (U) of *botulinum* toxin is defined as the $LD_{50}$ upon intraperitoneal injection into female Swiss Webster mice weighing 18 to 20 grams each.

*Botulinum* toxin has become widely investigated for its therapeutic potential in the treatment of a variety of neuromuscular disorders including: blepharospasm, spasmodic dysphonia, Strabismus, hemifacial spasm, and adult onset spasmodic torticollis. (Simpson, 1981; Habermann, 1989; Jankovic and Brin, 1991; Borodic et al., 1991; Hambleton, 1992; Schantz and Johnson, 1992; Valtorta and Arslan 1993). Intramuscular injection of nanogram quantities of purified *botulinum* toxin results in the toxin binding to presynaptic cholinergic nerve terminals and inhibits the release of acetylcholine and thus decreases muscle activity. The result is relaxation of the tonically contracted muscle and thus relaxation of the intended muscle or muscle group.

*Botulinum* toxin has been described in a method for treating osteoarthritis associated pain (see e.g. U.S. Pat. No. 8,470,337); wherein the toxin is administered by intramuscular injections into the splenius capitis and temporalis muscles in order to alleviate the osteoarthritis associated pain.

The present disclosure provides a method for treating or alleviating osteoarthritis associated-symptoms in a patient in need thereof. In some embodiments, the osteoarthritis associated-symptom is joint pain.

In some aspects, the present disclosure provides a method for treating or alleviating OA-associated pain, the method comprises selecting a treatment-susceptible or treatment-eligible patient, and administering to the treatment-eligible patient a therapeutically effective amount of a clostridial derivative to an osteoarthritis-affected site of the patient, thereby treating or alleviating the OA-associated pain. In some embodiments, the treatment-eligible patient is one whose pain has been categorized as nociceptive.

In some embodiments, the selecting step comprises categorizing the pain that a patient experiences at an osteoarthritis-affected site.

In some embodiments, the categorizing step comprises classifying the pain that the patient experiences as nociceptive or non-nociceptive, such as neuropathic or possibly neuropathic.

In some embodiments, the categorizing step comprises providing to the patient a plurality of questions, the plurality of questions relating to the characteristics of the pain that the patient perceives. In some embodiments, the characteristics comprise the gradation of pain, the pain course pattern, the pain radiating pattern, or combinations thereof. In some embodiments, the plurality of questions comprise numerical values which the patient chooses to rate the characteristics of the pain. In some embodiments, one or more questions comprise selecting a picture that best describes the course of the pain. In some embodiments, the picture has a numerical value assigned. In some embodiments, at least one question comprises a confirmation or disconfirmation question, wherein the patient can reply with confirmation (yes) or disconfirmation (no). In some embodiments, the confirmation and disconfirmation replies are each assigned each a numerical value.

In some embodiments, the categorizing step further comprises receiving numerical responses to the plurality of questions from the patient, calculating a score based on the numerical responses from the patient.

In some embodiments, the selecting step comprises identifying the patient as treatment-susceptible/eligible or treatment-unsusceptible/ineligible. In some embodiments, the treatment-eligible patient is categorized as having nociceptive pain. In some embodiments, the treatment-ineligible patient is categorized as having non-nociceptive pain, such as neuropathic pain or possibly neuropathic pain.

In some embodiments, the identifying step comprises comparing the score calculated in the categorizing step with a cut-off value. In some embodiments, the patient is identified as treatment-eligible if the score is smaller or equal to the cut-off value. In some embodiments, the patient is identified as treatment-ineligible if the score is greater than the cut-off value. In alternative embodiments, the patient is identified as treatment-eligible if the score is greater or equal to the cut-off value, or as treatment-ineligible if the score is smaller than the cut-off value.

In some embodiments, the selecting step comprises identifying the patient as treatment-eligible, treatment-ineligible or treatment-uncertain. In some embodiments, the treatment-eligible patient is one categorized as having nociceptive pain. In some embodiments, the treatment-ineligible patient is one categorized as having neuropathic pain. In some embodiments, the treatment-uncertain patient is one that is categorized as having non-nociceptive pain, which is likely or probably neuropathic pain.

In some embodiments, the selecting step comprises comparing the score calculated in the categorizing step with two cut-off values. In some embodiments, the patient is identified as treatment-eligible if the score is smaller or equal to a first cut-off value. In some embodiments, the patient is identified as treatment-ineligible group if the score is greater or equal to a second cut-off value. In some embodiments, the patient is identified as treatment-uncertain if the score is greater than the first cut-off value and smaller than the second cut-off value. In alternative embodiments, the patient is identified as treatment-eligible if the score is greater or equal to the first cut-off value, as treatment-ineligible if the score is smaller than the second cut-off value, or treatment uncertain if the score is smaller than the first cut-off value and larger than the second cut-off value. In some embodiments, if the patient is identified as treatment-uncertain, additional assessment is carried out to further determine whether the patient is treatment-eligible or ineligible. In some embodiments, the present method comprises selecting a treatment-eligible patient. In some embodiments, the present method comprises excluding patients that are not identified as treatment-eligible, such as treatment-ineligible or treatment-uncertain.

In some embodiments, the present method comprises using a questionnaire to identify a treatment-eligible patient. Table 1 illustrates an exemplary and non-limiting questionnaire that can be used with the present method.

TABLE 1

Exemplary questionnaire to classify patients as treatment-eligible or treatment-ineligible.

| Item | Score |
|---|---|
| Gradataion of pain* | |
| Do you suffer from a burning sensation (e.g. stinging nettles) in the marked areas? | 0-5 |
| Do you have a tingling or prickling sensation in the area of your pain (like crawling ants or electrical tingling)? | 0-5 |
| Is light touching (clothing, a blanket) in this area painful? | 0-5 |
| Do you have sudden pain attacks in the area of your pain, like electric shocks? | 0-5 |
| Is cold or heat (bath water) in this area occasionally painful? | 0-5 |
| Do you suffer from a sensation of numbness in the areas that you marked? | 0-5 |
| Does slight pressure in this area, e.g. with a finger, trigger pain? | 0-5 |
| Pain course pattern | |
| Please select the picture that best describes the course of your pain: | |
|  Persistant pain with slight fluctuations | 0 |
|  Persistant pain with pain attacks | −1 |
|  Pain attacks without pain between them | +1 |
|  Pain attacks with pain between them | +1 |
| Radiating pain | |
| Does your pain radiate to other regions or your body? Yes/No | +2/0 |

*For each question never, 0; hardly noticed, 1; slightly, 2; moderately, 3; strongly, 4; very strongly, 5
Questions used to document pain, but which were not used in the scoring, are not shown In an exemplary and non-limiting embodiment, the present method comprises using a PainDETECT questionnaire (shown in Table 1) to select or identify a treatment-eligible patient. In some embodiments, the present method comprises using the PainDETECT questionnaire to classify patients into nociceptive or non-nociceptive groups.

In one exemplary embodiment, the PainDETECT questionnaire is a patient self-administered questionnaire. The questionnaire has a total minimum score of 1 and a total maximum score of 38, which is calculated from the sum of scores to nine questions, the questions relating to the gradation of pain, the pain course pattern, the pain radiating pattern, or combinations thereof. In some embodiments, the patient is identified: (1) as having nociceptive pain if the total score to the questionnaire is smaller or equal to a cut-off point; or (2) as having non-nociceptive pain group if the total score to the questionnaire is greater than the cut-off point. The cut-off value can be any number within the total minimum score and the total maximum score. In some embodiments, the cut-off value is 12. In alternative embodiments, the patient is identified: (1) as having nociceptive pain if the total score to the questionnaire is smaller or equal to a first cut-off point; (2) as having non-nociceptive pain group if the total score to the questionnaire is greater or equal than a second cut-off point; or (3) as having possibly non-nociceptive pain if the total score is greater than the first cut-off point and smaller than the second cut-off point. The cut-off value can be any number within the total minimum score and the total maximum score. In some embodiments, the first cut-off value is 12 and the second cut-off value is 19. In alternative embodiments, the first cut-off value and the second cut-off values can be different numbers.

In some embodiments, subsequent to the selecting step, the present method comprises administering to the treatment-eligible patient a therapeutically effective amount of a clostridial derivative to an osteoarthritis-affected site.

In some embodiments, the arthritis-affected site or osteoarthritis-affected site includes a knee joint, a hip joint, a hand joint, a shoulder joint, an ankle joint, a foot joint, an elbow joint, a wrist joint, a sacroiliac joint, a spine joint, or combinations thereof.

In some embodiments, the clostridial derivative is administered directly into a joint cavity or structural components surrounding the joint cavity, or both. In some embodiments, the administration of the clostridial derivative is by intra-articular, extra-articular, peri-articular injections, or combinations thereof. In one embodiment, the clostridial derivative is administered in the patellofemoral space of the study knee, using an aseptic and ultrasound guided technique.

Intra-articular administration sites include the cavity of the affected joint, a medial supra-patellar portal, medial or lateral mid-patellar portals and medial or lateral infra-patellar portals, or combinations thereof. Peri-articular delivery sites include: infra-patellar fat pad, quadriceps fat pad, anterior suprapatellar fat pad, subcutaneous space, subcutaneous bursa, intra-articular bursa, cruciate ligaments if present, menisci if present, medial and/or lateral collateral ligaments, capsule, periosteum in the joint, bone morrow; tendons surrounding the joint; intra-venous infusion. In alternative embodiments, the administration route is by intramuscular, non-intramuscular, intradermal, subcutaneous administration, intrathecal administration, intraperitoneal administration, implantation, or combinations thereof.

Intra-articular administration of the clostridial derivative to the affected site can be guided by fluoroscopy or ultrasonography, as well known to one of ordinary skills in the art. For deeper joints such as the hip, imaging guidance is crucial. To limit the risk of inaccurate needle placement, the present method further comprises aspirating synovial fluid within the joint cavity prior to administration of the clostridial derivative.

In some embodiments, the clostridial derivative of the present method includes a native, recombinant clostridial toxin, recombinant modified toxin, fragments thereof, targeted exocytosis modulators (TEMs), or combinations thereof. In some embodiments, the clostridial derivative is a *botulinum* toxin. In alternative embodiments, the clostridial derivative is a TEM.

In some embodiments, the *botulinum* neurotoxin can be a modified neurotoxin, that is a *botulinum* neurotoxin which has at least one of its amino acids deleted, modified or replaced, as compared to a native toxin, or the modified *botulinum* neurotoxin can be a recombinant produced *botulinum* neurotoxin or a derivative or fragment thereof. In certain embodiments, the modified toxin has an altered cell targeting capability for a neuronal or non-neuronal cell of interest. This altered capability is achieved by replacing the naturally-occurring targeting domain of a *botulinum* toxin with a targeting domain showing a selective binding activity for a non-*botulinum* toxin receptor present in a non-*botulinum* toxin target cell. Such modifications to a targeting domain result in a modified toxin that is able to selectively bind to a non-*botulinum* toxin receptor (target receptor) present on a non-*botulinum* toxin target cell (re-targeted). A modified *botulinum* toxin with a targeting activity for a non-*botulinum* toxin target cell can bind to a receptor present on the non-*botulinum* toxin target cell, translocate into the cytoplasm, and exert its proteolytic effect on the SNARE complex of the target cell. In essence, a *botulinum* toxin light chain comprising an enzymatic domain is intracellularly delivered to any desired cell by selecting the appropriate targeting domain.

In some embodiments, the clostridial derivative is a *botulinum* toxin, which is selected from the group consisting of *botulinum* toxin types A, B, $C_1$, D, E, F and G. In one embodiment, the clostridial derivative of the present method is a *botulinum* toxin type A. The *botulinum* toxin can be a recombinant *botulinum* neurotoxin, such as *botulinum* toxins produced by *E. coli*.

The clostridial derivative, such as a *botulinum* toxin, for use according to the present invention can be stored in lyophilized, vacuum dried form in containers under vacuum pressure or as stable liquids. Prior to lyophilization the *botulinum* toxin can be combined with pharmaceutically acceptable excipients, stabilizers and/or carriers, such as, for example, albumin, or the like. Acceptable excipients or stabilizers include protein excipients, such as albumin or gelatin, or the like, or non-protein excipients, including poloxamers, saccharides, polyethylene glycol, or the like. In embodiments containing albumin, the albumin can be, for example, human serum albumin or recombinant human albumin, or the like. The lyophilized material can be reconstituted with a suitable liquid such as, for example, saline, water, or the like to create a solution or composition containing the *botulinum* toxin to be administered to the patient.

In some embodiments, to increase the resident time of the clostridial derivative in the joint, the clostridial derivative is provided in a controlled release system comprising a polymeric matrix encapsulating the clostridial derivative, wherein fractional amount of the clostridial derivative is released from the polymeric matrix over a prolonged period of time in a controlled manner. Controlled release neurotoxin systems have been disclosed for example in U.S. Pat. Nos. 6,585,993; 6,585,993; 6,306,423 and 6,312,708, each of which is hereby incorporated by reference in its entirety.

The therapeutically effective amount of the clostridial derivative, for example a *botulinum* toxin, administered according to the present method can vary according to the potency of the toxin and particular characteristics of the condition being treated, including its severity and other various patient variables including size, weight, age, and responsiveness to therapy. The potency of the toxin is expressed as a multiple of the $LD_{50}$ value for the mouse, one unit (U) of toxin being defined as being the equivalent amount of toxin that kills 50% of a group of 18 to 20 female Swiss-Webster mice, weighing about 20 grams each.

The therapeutically effective amount of the *botulinum* toxin according to the present method can vary according to the potency of a particular *botulinum* toxin, as commercially available *Botulinum* toxin formulations do not have equivalent potency units. For example, one unit of BOTOX® (onabotulinumtoxinA), a *botulinum* toxin type A available from Allergan, Inc., has a potency unit that is approximately equal to 3 to 5 units of DYSPORT® (abobotulinumtoxinA), also a *botulinum* toxin type A available from Ipsen Pharmaceuticals. In some embodiments, the amount of abobotulinumtoxinA, (such as DYSPORT®), administered in the present method is about three to four times the amount of onabotulinumtoxinA (such as BOTOX®) administered, as comparative studies have suggested that one unit of onabotulinumtoxinA has a potency that is approximately equal to three to four units of abobotulinumtoxinA. MYOBLOC®, a *botulinum* toxin type B available from Elan, has a much lower potency unit relative to BOTOX®. In some embodiments, the *botulinum* neurotoxin can be a pure toxin, devoid of complexing proteins, such as XEOMIN® (incobotulinumtoxinA). One unit of incobotulinumtoxinA has potency approximately equivalent to one unit of onabotulinumtoxinA. The quantity of toxin administered and the frequency of its administration will be at the discretion of the physician responsible for the treatment and will be commensurate with questions of safety and the effects produced by a particular toxin formulation.

In some embodiments, the present method comprises administering a therapeutically effective amount of the clostridial derivative to the osteoarthritis-affected site. In some embodiments, the therapeutically effective amount is administered in multiples treatment sessions. In some embodiments, the therapeutically effective amount is administered per treatment session.

In some embodiments, the therapeutically effective amount ranges from about 2 units to about 800 units of a *botulinum* toxin type A, such as onabotulinumtoxinA (such as BOTOX®). In some embodiments, the therapeutically effective amount ranges from 10 units to about 100 units of onabotulinumtoxinA. In some embodiments, the therapeutically effective amount ranges from about 150 to about 300 units of onabotulinumtoxinA. In one embodiment, the therapeutically effective amount is about 200 units of onabotulinumtoxinA. In some embodiments, the therapeutically effective amount ranges from about 300 to about 500 units of onabotulinumtoxinA. In one embodiment, the therapeutically effective amount is about 400 units of onabotulinumtoxinA. In some embodiments, the therapeutically amount ranges from about 500 units to about 800 units of onabotulinumtoxinA.

In some embodiments, the therapeutically effective amount of abobotulinumtoxinA, (such as DYSPORT®), administered according to aspects of the present method is about three to four times the amount of onabotulinumtoxinA (such as BOTOX®). In some embodiments, the therapeutically effective amount of incobotulinumtoxinA, (such as XEOMIN®), administered according to aspects of the present method is similar to the amount of onabotulinumtoxinA (such as BOTOX®) administered, as comparative studies have suggested that one unit of incobotulinumtoxinA has a potency approximately equivalent to one unit of onabotulinumtoxinA.

In some embodiments, the therapeutically effective amount is from about 0.1 to 1000 micrograms (µg) of a TEM (Targeted Exocytosis Modulators).

In some embodiments, the present method comprises administering from about 2 to about 800 units of a *botulinum* toxin type A, such as BOTOX®, intra-articularly into a joint space, such as for example a knee joint. In some embodiments, the present method comprises administering 50-250 units of onabotulinumtoxinA, such as BOTOX, intra-articularly into a joint space. In one specific embodiment, the present method comprises administering about 200 units of a *botulinum* toxin type A intra-articularly into a joint space. In one specific embodiment, the present method comprises administering about 400 units of a *botulinum* toxin type A intra-articularly into a joint space. In some embodiments, the present method comprises administering about 10-500 units of a *botulinum* toxin type A into a fat pad, such as the infra-patellar fat pad, the supra-patellar fat pad, or combinations thereof. In one specific embodiment, the present method comprises administering about 10-500 units of a *botulinum* toxin type A intra-articularly into a joint space and about 10-500 units into a fat pad, such as the infra-patellar fat pad, the supra-patellar fat pad, or combinations thereof. In alternative embodiments, the present method comprises administering about 40-1200 units of DYSPORT® intra-articularly into a joint space and about 40-2000 units of DYSPORT® into a fat pad, such as the infra-patellar fat pad, the supra-patellar fat pad, or combinations thereof. In some embodiments, the present method comprises administering a *botulinum* toxin type A, and concurrently or sequentially administering a *botulinum* toxin type B, $C_1$, D, E, F, G, or combinations thereof. In alternative embodiments, the present method comprises administering a *botulinum* toxin type B, $C_1$, D, E, F, G, or combinations thereof.

In some embodiments, the present method comprises administering about 0.1 to 1000 micrograms (µg) of a TEM (Targeted Exocytosis Modulators) intra-articularly into a joint space, such as for example a knee joint. In some embodiments, the present method comprises administering about 20-250 µg of TEM intra-articularly into a joint space. In one specific embodiment, the present method comprises administering about 3-70 µg of TEM intra-articularly into a joint space. In some embodiments, the present method comprises administering about 0.1 to 1000 µg of a TEM into a fat pad, such as the infra-patellar fat pad, the supra-patellar fat pad, or combinations thereof. In one specific embodiment, the present method comprises administering about 0.1 to 1000 µg of a TEM intra-articularly into a joint space and about 0.1 to 1000 µg into a fat pad, such as the infra-patellar fat pad, the supra-patellar fat pad, or combinations thereof.

The effects of the present method can persist for between about 1 month and 5 years. Administration can be modified according to the changes in OA-associated symptoms. In some embodiments, administration of a clostridial derivative according to aspects of the present method is carried out from about 3 months to about 6 months. In some embodiments, increased efficacy of the treatment accorded to the present method is expected to happen when the clostridial derivative is administered according to the disclosed method at about 3 month intervals. In alternative embodiments, the present method can be repeated every 6 months, or 12 months, or 18 months according to progression of osteoarthritis.

In some embodiments, in addition to administering a therapeutically effective amount of a clostridial derivative to an OA-affected site, the present method further comprises administering corticosteroids and/or viscosupplements to the OA-affected site. Corticosteroids suitable for the present method includes methylprednisone acetate (DEPO-MEDROL), triamcinolone acetate (KENALOG 10, KENALOG 40), triamcinolone hexacetonide (ARISTOSPAN).Viscosupplements suitable for the present method include hyaluronate formulations, such as ADANT®, SYNOCROM® or SYNVISC®. The corticosteroids and/or viscosupplements can be administered concurrently, prior to and/or subsequent to the administration of the clostridial derivative. Viscosupplements administration to restore elastoviscosity of the joint (dosage, frequency, and mode) can be carried out as well known to one of ordinary skill in the art.

The following non-limiting examples provide those of ordinary skill in the art with specific preferred methods to treat or alleviate osteoarthritis-associated symptoms within the scope of the present disclosure, and it is not intended to limit the scope of the invention. In the following examples various modes of non-systemic administration of a *botulinum* neurotoxin can be carried out. For example, by intramuscular injection, non-intramuscular injection, intra-articular injection, extra-articular injection, peri-articular injection, subcutaneous injection or by implantation of a controlled release implant.

EXAMPLES

The following non-limiting examples provide those of ordinary skill in the art with specific preferred methods to treat conditions within the scope of embodiments of the present invention and are not intended to limit the scope of the invention.

Example 1

*Botulinum* Toxin Therapy for Osteoarthritis (OA) Knee Pain

A double-blind, placebo-controlled, randomized study was performed to evaluate the efficacy of a single intra-articular (IA) injection of a *botulinum* toxin Type A (such as BOTOX®) compared with placebo for treatment for primary idiopathic knee osteoarthritis (OA) (Kellgren-Lawrence (KL) grade I, II or III). Participants were men or women aged 40 to 75 years (N=121).

The patients were randomized in the treatment group or the placebo group. Two analysis populations were defined: the safety population and intent-to-treat (ITT) population. The safety population consisted of all patients who received at least 1 injection of the study treatment. For the safety population, patients were analyzed according to actual treatment received at the study treatment visit, regardless of randomization assignment. The ITT population consisted of all randomized patients, whether treated or not. For the ITT population, patients were to be analyzed according to randomization assignment, regardless of actual treatment received. The safety population was used for analysis of safety variables, as well as efficacy variables and for other variables that were not safety variables.

There were no clinically relevant differences in baseline characteristics. Mean age 62.3 years, 51% female, all Caucasian, KL I=9.1%: KL II=62%; KL III=28.9%.

At the baseline, the patients were given a PainDETECT questionnaire (PD-Q). An exemplary questionnaire is shown in table 1. The total score (range from -1 to 38) was calculated from the sum of score to nine questions. The Baseline PainDETECT scores were used post-hoc to classify patients into three groups. The following cut-off points were used:

Score≤12: nociceptive pain (neuropathic component unlikely)
Score 13-18: neuropathic pain possible
Score≥19: neuropathic pain (nerve lesion or dysfunction likely)

Study design: For the treatment group, a single 200 U dose of a *botulinum* toxin Type A (BOTOX®) was injected into the intra-articular space of the knee on Day 1. For the placebo group, a single dose of normal saline was injected into the intra-articular space of the study knee on Day 1.

The primary efficacy variable was the change from baseline of the average over 14 days of the daily worst pain score. The 14-day average score was derived from daily scores recorded in a diary for worst pain in the study knee. Cumulative 14-day pain scores were prorated or imputed if necessary, with the average calculated from the cumulative scores.

The secondary efficacy variables included change from baseline in the Western Ontario McMaster (WOMAC) Osteoarthritis Index and change in baseline in the patient global impression of change (patient-GIC). The following scores from the WOMAC were obtained at the baseline and at each follow-up visit: Total Index Score; Pain Score, Physical Function Score.

The Patient-GIC is a questionnaire used by the patient to provide a global impression of change in their health status since enrollment, whether or not in the patient's judgment a change was related to the study treatment. The patient-GIC score was obtained at each follow-up visit, which is a change from baseline by definition on a −3 and +3 scale. Response on the patient-GIC was on a −3 to +3 scale of very much worse, much worse, minimally worse, no change, minimally improved, much improved, and very much improved. Negative scores indicate worsening and positive scores indicate improvement. Responder analyses were performed on patient-GIC by visit at weeks 1, 4, 8, and 12. A patient was considered a responder at a particular visit if the response of the patient-GIC was 'much improved' or 'very much improved' at that visit.

Other efficacy measurements included: physician global impression of change (physician-GIC), rescue medication count and PainDETECT Questionnaire (PD-Q), knee synovial fluid effusion biomarker concentrations and pain models.

Rescue Medication Count: Rescue medication cumulative count, per 14-day baseline and changes from baseline to the 14-day periods ending with each week starting with week 2 were analyzed. Each 14-day cumulative count was derived from daily responses recorded in the diary regarding the number of paracetamol tablets used.

Pain Model Evaluations:

There were 5 sets of efficacy variables derived from pain model evaluations:

quantitative sensory testing (QST) of joint pain, as indicated by pressure-pain threshold (PPT)
spreading sensitization, as indicated by PPT
spreading sensitization, as indicated by area of pain in the knee
wind-up like pain, assessed on the study knee for the most painful knee site
cuff algometry, involved 3 variables, the cuff pressure, pressure-pain tolerance, and the pressure-pain limit, with each of the 3 variables represented by the mean of 3 repeat measurements.

Results: For the overall safety population, no significant difference in outcome and pain relief between the treatment group and the placebo group. The nociceptive patients (n=68) showed improved outcomes in the PPT pain model and wind-up like pain model, along with pain relief following treatment with *botulinum* toxin type A (BOTOX®) versus placebo.

Since the safety population and the ITT population were identical in this study, results are summarized for the safety population and are applicable to the ITT population.

Figure 1:
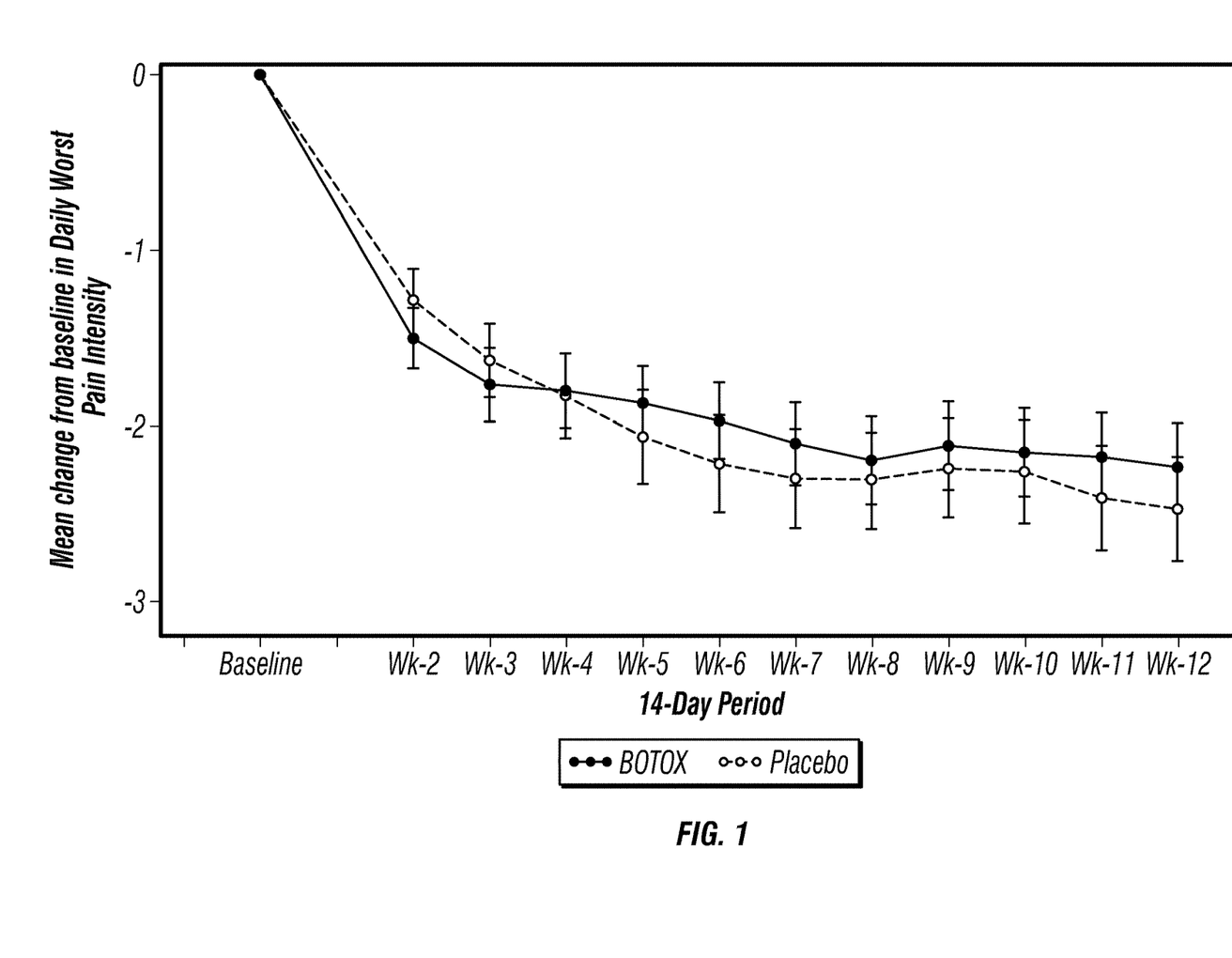
FIG. 1 shows the mean change from baseline in Daily Worst Pain Intensity per 14-Day Period in the overall or safety population after treatment with an exemplary clostridial derivative (onabotulinumtoxinA) or with a placebo in patients with primary knee osteoarthritis. Baseline refers to the Pain Intensity recorded the last 14 days preceding randomization. Each week-X refers to the 14 day period ending with that post-treatment week.
Figure 3A:
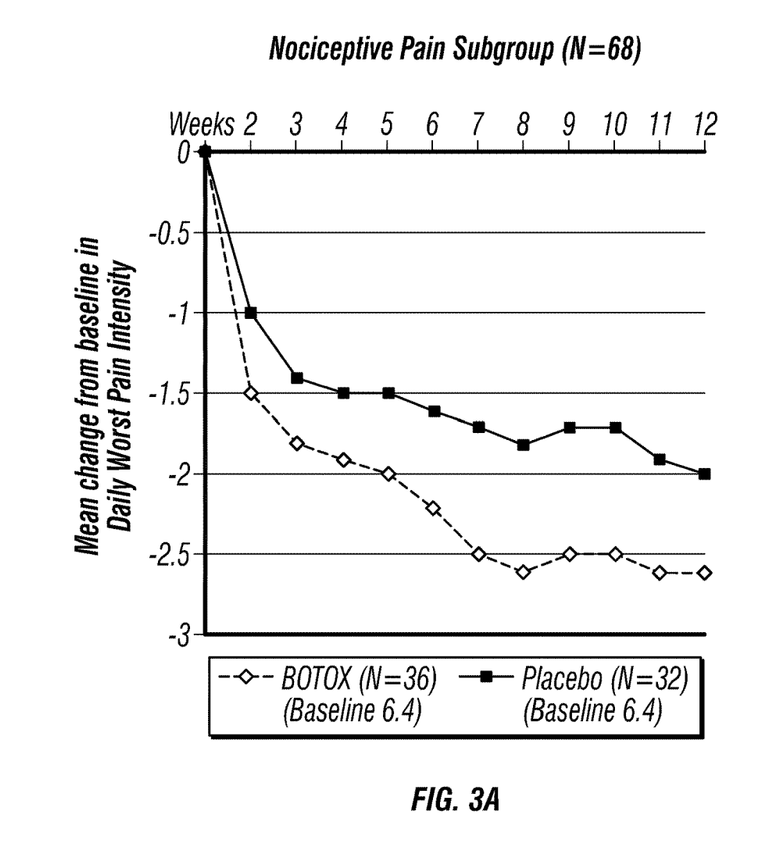
FIGS. 3A and 3B show the mean change from baseline in Daily Worst Pain Intensity in a nociceptive pain subgroup (3A) and the overall safety population (3B) over 12-week period after treatment with the exemplary clostridial derivative or with the placebo in patients with primary knee osteoarthritis.
Figure 3B:
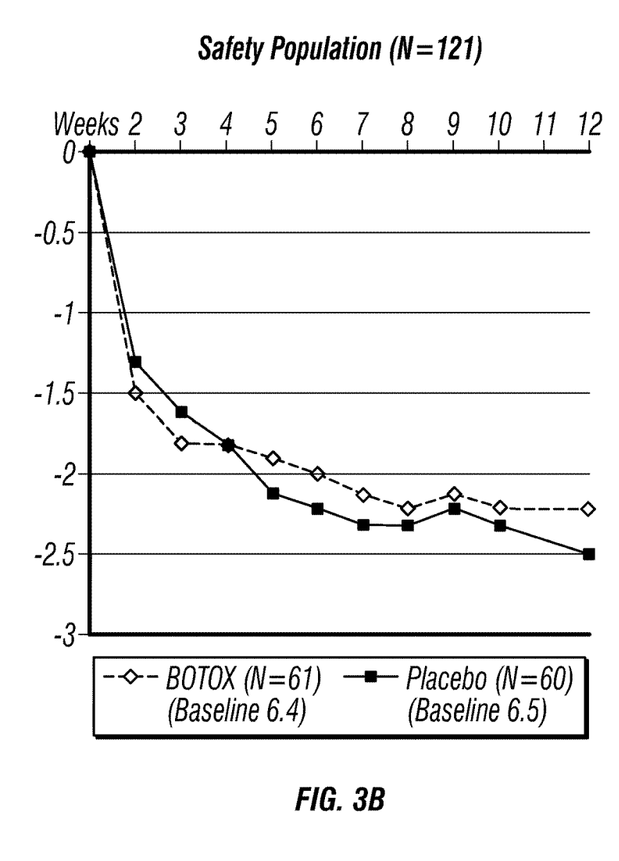

As shown in FIGS. 1 and 3B, for the overall safety population, no statistically significant difference between the treatment group and the placebo group was observed in the daily worst pain score.

Figure 2:
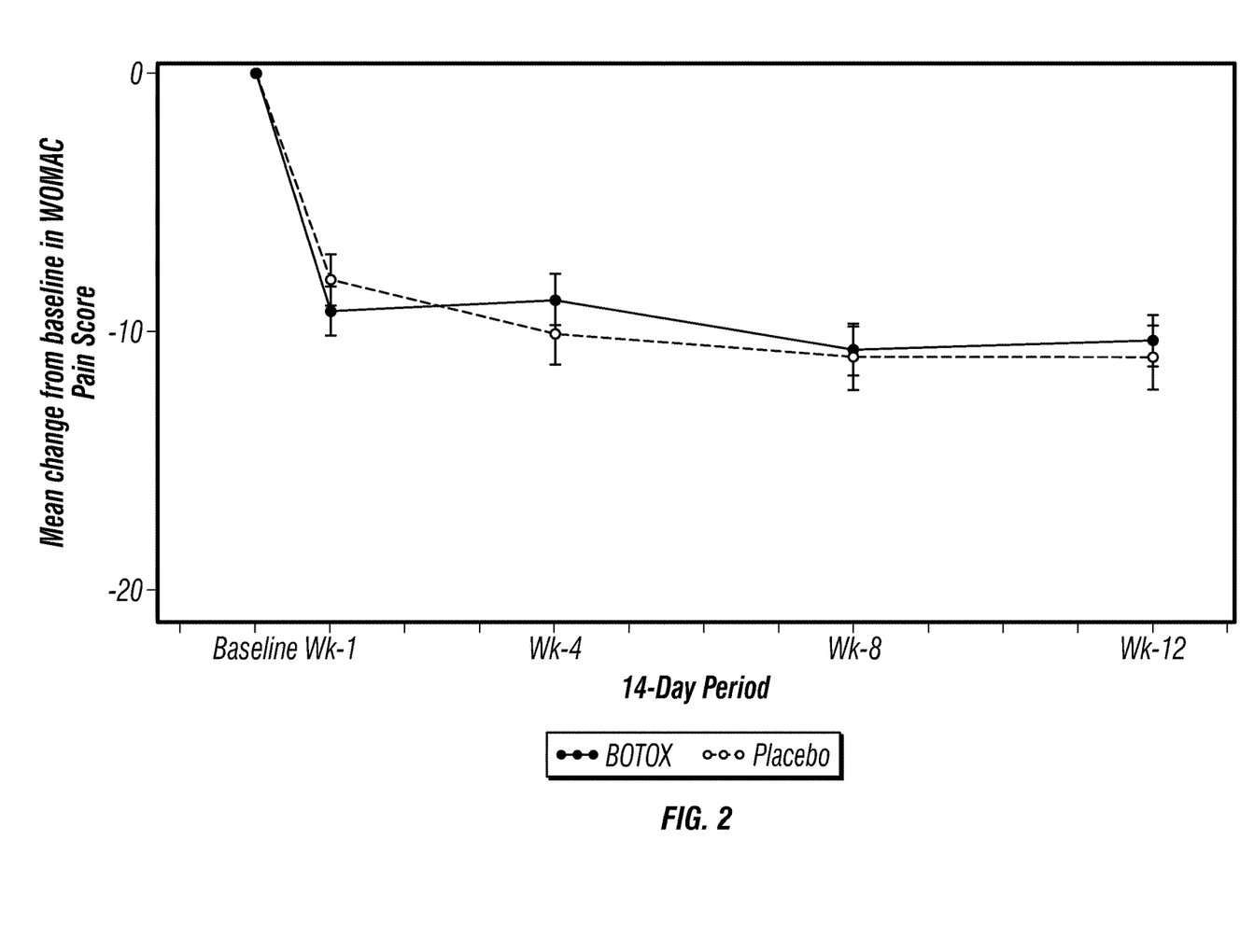
FIG. 2 shows the mean change from baseline in WOMAC Pain Score in the overall safety population over 12-week period after treatment with the exemplary clostridial derivative or with the placebo in patients with primary knee osteoarthritis. Baseline refers to the Pain Score recorded on Day 1 prior to treatment.
Figure 4A:
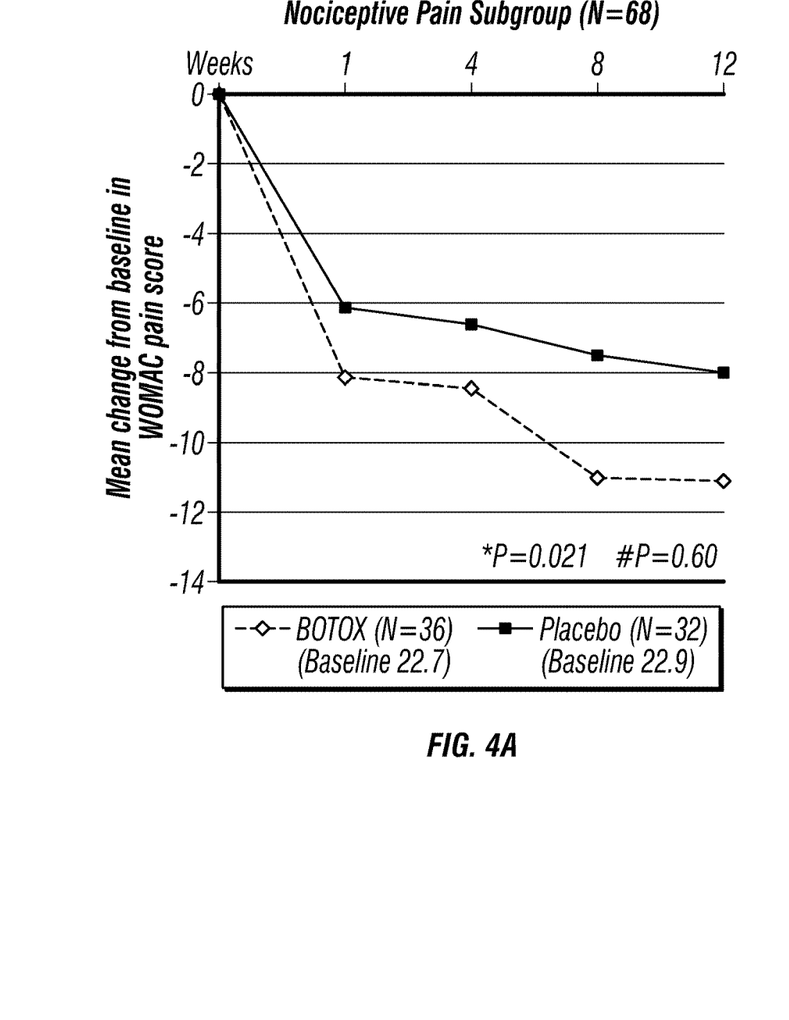
FIGS. 4A and 4B show the mean change from baseline in WOMAC pain score in the nociceptive pain subgroup (4A) and the overall safety population (4B) over 12-week period after treatment with the exemplary clostridial derivative or with the placebo in patients with primary knee osteoarthritis.
Figure 4B:
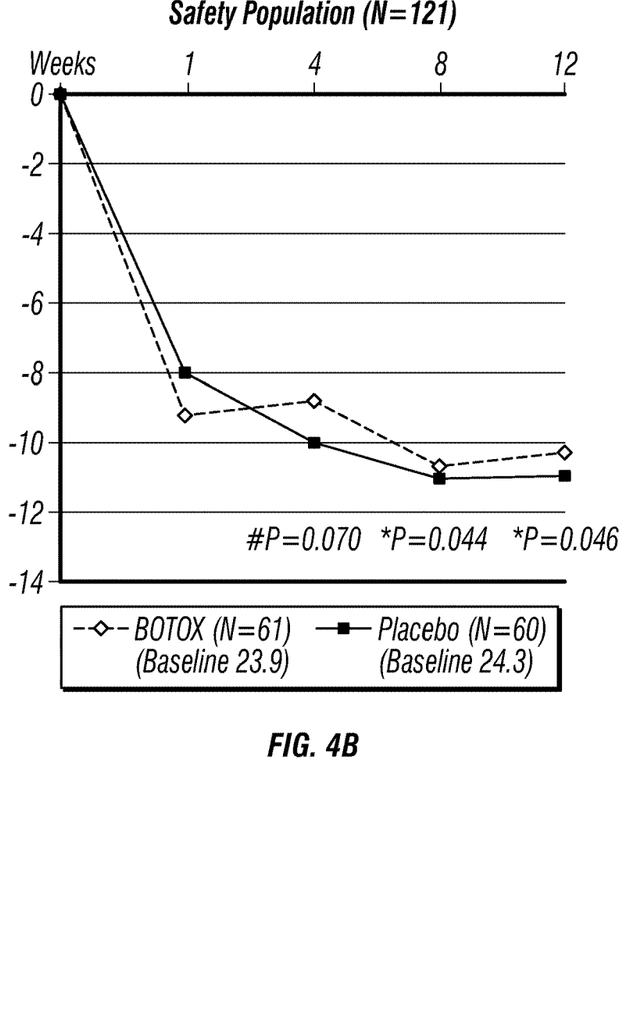

As shown in FIGS. 2 and 4B, for the overall safety population, no statistically significant differences were observed between the treatment group and the placebo group in the change from baseline in the WOMAC Pain scores. Similarly, for the overall safety population, no statistically significant differences between the treatment group and the placebo group were observed in the change from baseline in the WOMAC total index score, WOMAC physical function score.

Figure 5A:
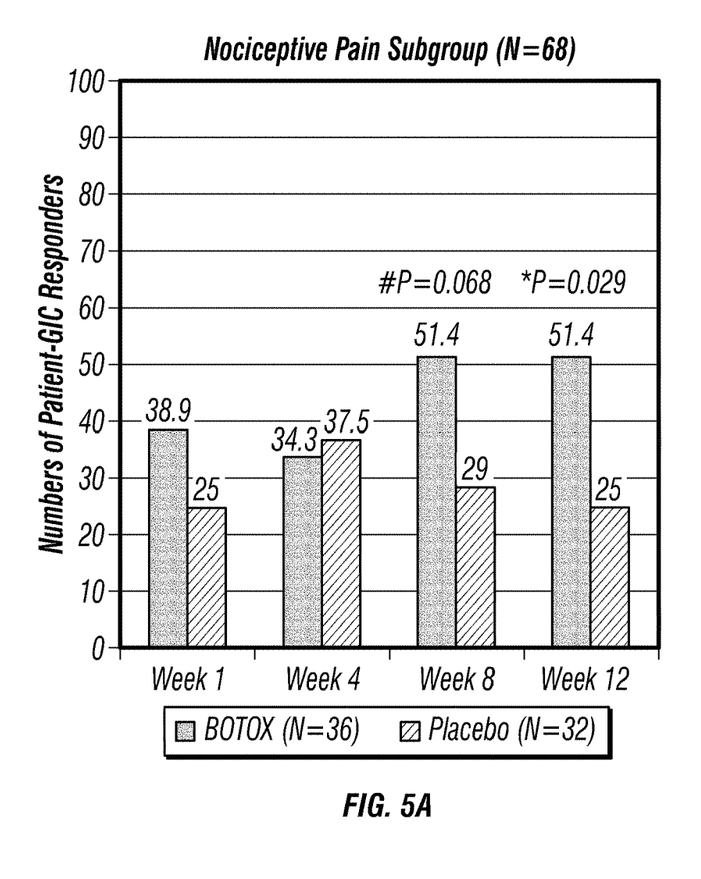
FIGS. 5A and 5B show the numbers of Patient-GIC Responders in the nociceptive pain subgroup (5A) and the overall safety population (5B) over 12-week period after treatment with the exemplary clostridial derivative or with the placebo in patients with primary knee osteoarthritis.
Figure 5B:
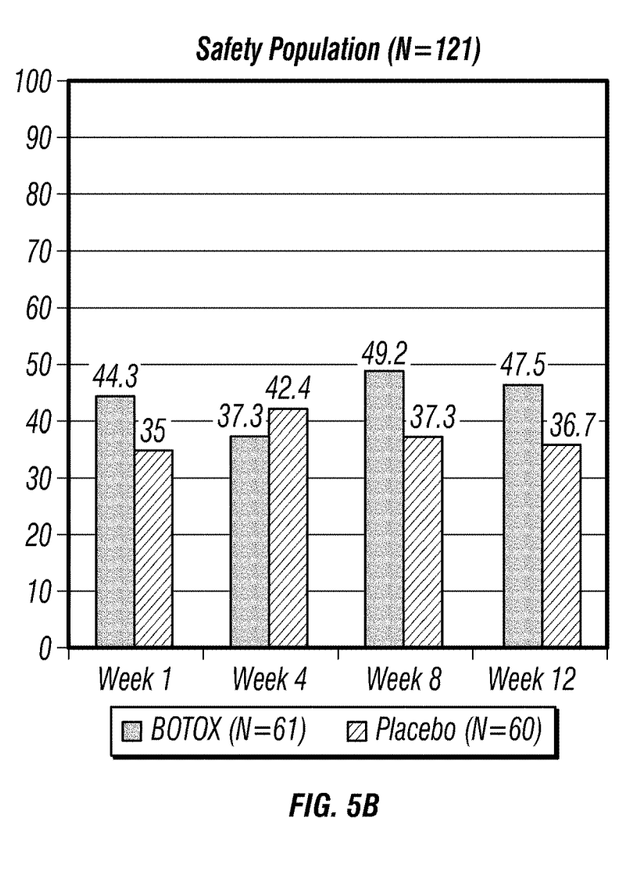

As shown in FIG. 5B, for the overall safety population, no statistically significant differences were observed between the treatment group and the placebo group in the patient-GIC responder. Even though no statistically significant differences were observed between the treatment and the placebo groups in the GIG-responder rate in the safety population, the responder rate was higher in the treatment group than in the placebo group at weeks 1, 8, and 12. The responder rates at weeks 8 and 12 were 29/59 (49.2%) and 28/59 (47.5%), respectively, in the treatment group and were 22/59 (37.3%) and 22/60 (36.7%), respectively, in the placebo group.

Of the 121 patients in the safety population, 68 patients were in the nociceptive pain subgroup; 36 patients in the BOTOX group and 32 patients in the placebo group. The demographics and baseline characteristics of the nociceptive pain subgroup were similar to the safety population with no clinically relevant or statistically significant differences observed between the treatment groups. In the nociceptive pain subgroup, the mean age of patients was 62.0 years (62.3 years in the safety population), 51.5% (35/68) were in the 40 to 64 years age subgroup, and 48.5% (33/68) were in the ≥65 years age subgroup.

As shown in FIG. 3A, for the nociceptive pain subgroup, at any time point, the treatment group had a numerically greater (improvement) mean change from baseline than the placebo group.

As shown in FIG. 4A, in the nociceptive pain subgroup, the mean (SD) WOMAC pains cores at baseline were 22.7(5.95) and 22.9 (6.98) in the treatment and placebo groups, respectively. At the follow up visits weeks 1, 4, 8 and 12, there was a decrease (improvement) in the WOMAC pain score in both treatment and placebo groups. The decrease in WOMAC pain score was numerically greater in the treatment group than in the placebo group at all follow-up visits and statistically significantly greater at week 8 (p = 0.021).

As shown in FIGS. 5A and 5B, the difference in patient-GIC responders was more significant between the treatment versus placebo groups in the nociceptive patient population relative to the overall safety population. Indeed, the differences in the patient-GIC responders between the treatment group and the placebo group in the overall safety population for weeks 1, 4, 8 and 12 were 27%, -12%, 32% and 29% respectively. In contrast, for the nociceptive patient group, as shown in FIG. 5A, the differences in patient-GIC score between the treatment group and the placebo group in the total population for weeks 1, 4, 8 and 12 were 56%, -8%, 77% and 106%, respectively.

Figure 6A:
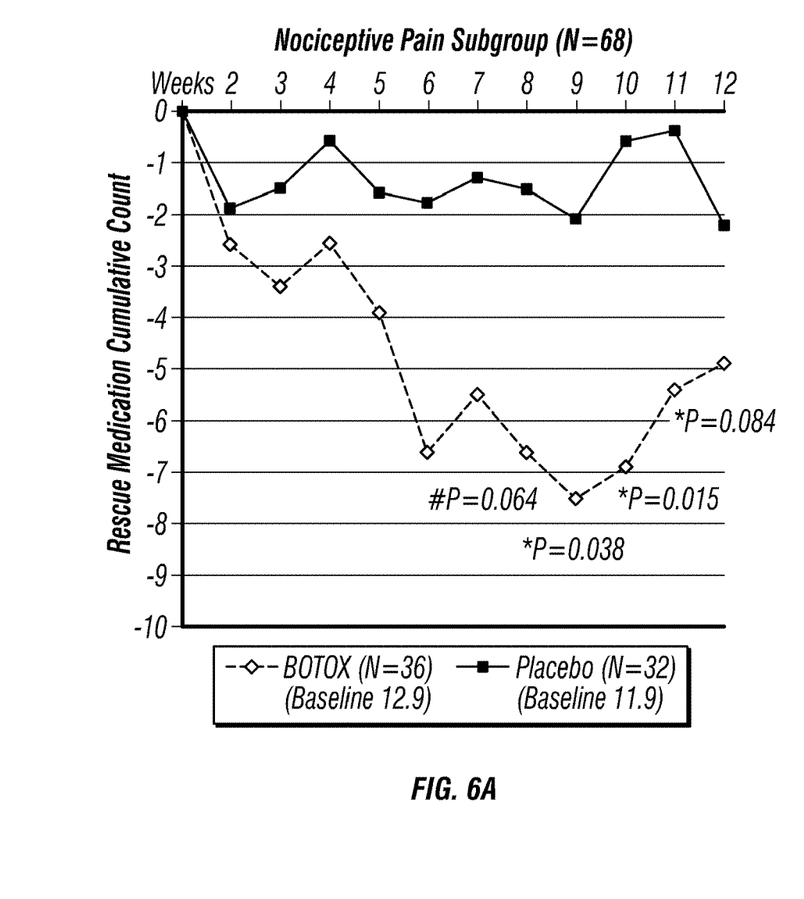
FIGS. 6A and 6B show the Rescue Medication Cumulative Count in the nociceptive pain subgroup (6A) and the overall safety population (6B) over 12-week period after treatment with the exemplary clostridial derivative or with the placebo in patients with primary knee osteoarthritis.
Figure 6B:
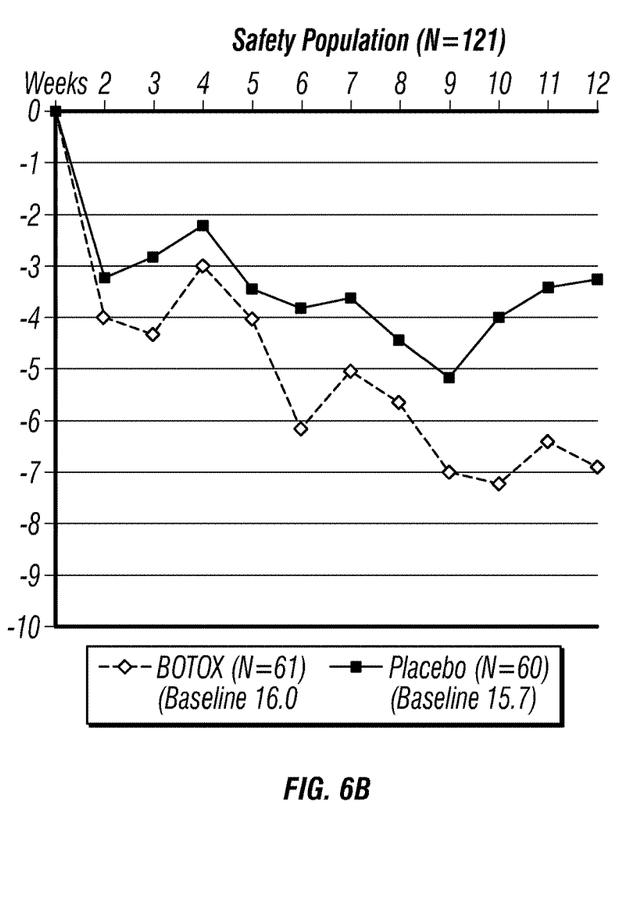

As shown in FIG. 6B, the mean reduction from baseline in number of medication days per 14-day period was greater in the BOTOX group than in the placebo group at all weeks. Statistically significant between group differences in favor of BOTOX were observed from week 9 to week 12 in the mean change from baseline in medication days per 14-day period. As shown in FIGS. 6A and 6B, the difference in Rescue Medication Cumulative Count was more significant between the treatment group versus placebo in the nociceptive patient subgroup, versus the overall safety population.

Example 2

Effect of *Botulinum* Toxin Type A (BOTOX®) Treatment on OA Knee Pain

A 42 year old male, with a body weight of 86kg and a height of 1.82m, had been suffering from left knee pain for over 4 years. He was diagnosed with knee osteoarthritis, without any apparent knee trauma or surgery. Administrations of acetaminophen and NSAIDs failed to alleviate the pain, which severely limited his activities. X-ray rating showed that this patient's knee joint had Kellgren-Lawrence score of I (indicating formation of osteophytes on the tibial spines). He expressed his willingness to participate in a BOTOX knee osteoarthritis trial. His mean daily worst pain was 7.8 numerical rating scale (or NRS) for the 14-day period prior to treatment. The patient was provided a pain-DETECT questionnaire at the screening. The score of his questionnaire was found to be 11.

The patient was treated with 200 units of a *botulinum* toxin Type A (BOTOX®) by intra-articularly injection in the knee joint under ultra-sound guidance.

The patient did not have any discomfort post injection. After one week, the patient reported that his knee pain via NRS was reduced from 7.8 to 6.3. His pain continued to improve, by the end of the 12 week study he rated his knee pain as 2.0 on the NRS; thus his total NRS pain reduction was 5.8. It has been established that a NRS improvement of at least 2.0 is clinical meaningful. He also reported that with the pain alleviated, he was able to resume his daily activities with much less limitation.

Example 3

A 47 year old female, with a body weight of 87 kg and a height of 1.6 m, had been suffering from left knee pain for over 4 years. She was diagnosed with idiopathic knee osteoarthritis. She had been treated with NSAIDs, intra-articular steroids or hyaluronic injections. However, these treatments failed to provide sufficient pain relief and functional improvement. She was willing to participate in the knee OA clinical trial. Her mean daily worst pain score was 5.9 NRS at baseline (the mean of 14-day pain scores). She was also provided a PainDETECT questionnaire. Her total score to the questionnaire was found to be 12.

She was treated with about 200 units of a *botulinum* toxin Type A (BOTOX) into the knee joint by intra-articular injection. No post injection discomfort was reported. After one week, the patient reported pain relief, her pain rating was 4.6 via NRS. After the 12 week study, her pain score was 3.6 via NRA by the end of the study with a total pain reduction of 2.3. It has been established that a NRS improvement of at least 2.0 is clinical meaningful.

Example 4

An active 34-year-old female who plays women ice hockey and is an avid weekend cyclist presents with right knee pain. Her physical therapist has used a variety of techniques including manipulation and stretches, which fail to resolve the pain. She takes simple anti-inflammatory medication to ease the pain; however they provide little relief. Her baseline NRS pain score is 7.0. She is provided with a PainDETECT Questionnaire to categorize her pain. Her total score is 10. She is determined to be treatment-susceptible. She is treated with 250 µg of a TEM intra-articularly into the knee joint. After one week, the symptoms started to improve with significant improvement observed at week 12. Her post-treatment NRS pain scores are reduced by 5.0 points, with a post treatment score at week 12 of 2.0 NRS. It has been established that a NRS improvement of 2.0 is clinical meaningful.

Example 6

A 57 year old mechanic reports to his doctor that pain due to the arthritis in his 1$^{st}$ carpometacarpal (CMC) joints of both hands and the base of the thumb joint cannot be flexed. The pain is becoming unbearable, and rates his pain at a 9 on the numerical rating scale (NRS) for pain at the doctor's office. Application of various topical creams that contain ingredients such as methyl salicylate, menthol and capsaicin are ineffective. The physician provides him with a questionnaire to categorize his pain and to determine whether he would be responsive to a *botulinum* toxin treatment. His total score is 8, which is deemed to be treatment-eligible. The physician decides to administer a *botulinum* toxin type A in order to treat the arthritis.

Upon ultrasound inspection, it is observed that effusion accumulates in the right $1^{st}$ CMC joint, which was withdrawn and stored at −80° C. The doctor administers a total of 100 units of a *botulinum* toxin type A (BOTOX) as follows: about 50 units into the right and left $1^{st}$ CMC joint cavity, respectively. After about 8 days, the patient reports that his arthritic pain is alleviated and ranks his pain at only a 2 on the same NRS. The arthritic pain remains alleviated for about at least about 3 months. There is no muscle weakness in his hands. He can use his hands for daily work now.

Example 7

A 39 year old female long distance runner (and known osteoarthritis sufferer) complains to her family doctor that her hip joints ache most of the time, and that her running regimen is being hampered by the pain, rating as an 8 on the doctor's NRS for pain. X-ray shows that her left hip joint space has moderate narrowing comparing with the right hip joint. She is diagnosed as hip osteoarthritis in both joints. After taking NSAIDs for 2 months, the patient reports that no improvement or alleviation of the pain. The physician provides her with a questionnaire to categorize the pain and to determine whether she would be responsive to a *botulinum* toxin treatment. The total score is 10, the patient is deemed to be treatment-eligible.

The doctor decides to treat the arthritis pain by administration of a *botulinum* toxin into hip joints. About 300 units of abobotulinumA (such as DYSPORT) are bilaterally injected, i.e. about 150 units into the left and right hip cavity in 2 mL normal saline. After 10 days, the patient reports returns to the doctor's office for a follow up and reports that the pain in her hips is alleviated, and now when asked to rate her pain, she rates it as a 3, a good and desirable improvement. The patient is similarly administered the *botulinum* toxin every 6 months thereafter. She can now resume her running activity. Her left hip joint space recovers to the normal level as her right hip joint space after *botulinum* toxin treatments.

Many alterations and modifications may be made by those having ordinary skill in the art, without departing from the spirit and scope of the disclosure. Therefore, it must be understood that the described embodiments have been set forth only for the purposes of examples, and that the embodiments should not be taken as limiting the scope of the following claims. The following claims are, therefore, to be read to include not only the combination of elements which are literally set forth, but all equivalent elements for performing substantially the same function in substantially the same way to obtain substantially the same result. The claims are thus to be understood to include those that have been described above, those that are conceptually equivalent, and those that incorporate the ideas of the disclosure.

We claim:

1. A method for treating or alleviating osteoarthritis (OA)-associated pain in a patient in need thereof, the method comprising identifying an OA patient whose pain has been categorized as nociceptive pain, and locally administering a therapeutically effective amount of a clostridial derivative to an osteoarthritis-affected site of the OA patient whose pain has been categorized as nociceptive pain, thereby treating or alleviating the osteoarthritis-associated pain in the patient, wherein the therapeutically effective amount is from about 200 units to about 800 units, wherein the clostridial derivative is onabotulinumtoxinA, and wherein the identifying comprises providing the OA patient a plurality of questions relating to characteristics of OA-associated pain that the patient perceives, receiving numerical responses to the questions by the patient, calculating a score based on the numerical responses, comparing the score to a cut-off value to categorize the OA-associated pain; and identifying the patient whose pain has been categorized as nociceptive pain.

2. The method of claim 1, wherein the osteoarthritis-affected site is selected from the group consisting of a knee joint, a hip joint, a hand joint, a shoulder joint, an ankle joint, a foot joint, an elbow joint, a wrist joint, a sacroiliac joint, a spine joint, and combinations thereof.

3. The method of claim 1, wherein the administering is by intra-articular injection into a joint space.

4. The method of claim 1, wherein the therapeutically effective amount ranges from about 300 to about 500 units of onabotulinumtoxinA.

5. The method of claim 1, wherein the therapeutically effective amount is about 400 units.

6. The method of claim 1, wherein the patient's pain is categorized as nociceptive when the score is smaller than or equal to the cut-off value.

7. The method of claim 1, wherein two cut-off values are used for the categorization.

8. The method of claim 7, wherein the patient's pain is categorized as nociceptive when the score is smaller than or equal to a first cut-off value, the patient's pain is categorized as non-nociceptive when the score is greater than or equal to a second cut-off value, and the patient's pain is categorized as uncertain when the score is greater than the first cut-off value and smaller than the second cut-off value.

* * * * *